United States Patent [19]

Schmitt, Jr. et al.

[11] 4,215,063

[45] Jul. 29, 1980

[54] OXIDATION CATALYST AND USE IN THE PRODUCTION OF ANTHRAQUINONE

[75] Inventors: Joseph L. Schmitt, Jr., Bethel; Hiei Ando, Stamford, both of Conn.

[73] Assignee: American Cyanamid Company, Stamford, Conn.

[21] Appl. No.: 35,664

[22] Filed: May 3, 1979

[51] Int. Cl.² ............................................. C09B 1/00
[52] U.S. Cl. .................................................... 260/369
[58] Field of Search ......................................... 260/369

[56] References Cited

U.S. PATENT DOCUMENTS

| | | | |
|---|---|---|---|
| 4,002,653 | 1/1977 | Reuter et al. | 260/369 |
| 4,036,860 | 7/1977 | Engelbach et al. | 260/369 |
| 4,036,861 | 7/1977 | Togo et al. | 260/369 |

*Primary Examiner*—Winston A. Douglas
*Assistant Examiner*—Raymond K. Covington
*Attorney, Agent, or Firm*—Bruce F. Jacobs

[57] ABSTRACT

Anthraquinone is prepared by the oxidation of diphenylmethane compounds in the gas phase in the presence of vanadium (V) oxide and a metal selected from ruthenium, rhenium, cerium, niobium and rhodium, and optionally a third metal selected from manganese, barium, cerium and iron.

15 Claims, No Drawings

OXIDATION CATALYST AND USE IN THE PRODUCTION OF ANTHRAQUINONE

The present invention relates to a process of preparing anthraquinone by oxidation of diphenylmethane compounds in the gas phase in the presence of vanadium (V) oxide and a second metal selected from ruthenium, rhenium, cerium, niobium, and rhodium and optionally a third metal selected from manganese, barium, cerium and iron.

U.S. Pat. No. 4,002,653 discloses the use of a catalyst system of vanadium pentoxide and titanium dioxide in a weight ratio of from 0.004:1 to 0.35:1 to perform the same reaction of the present invention. U.S. Patent 4,036,860 discloses an improvement over said earlier patent by incorporating into said catalyst a metal selected from tellurium, caesium, thallium and antimony.

There have been numerous other attempts at finding catalysts which will increase the yield of anthraquinone in the reaction. However, these have not been entirely satisfactory and research continues on ways to produce anthraquinone in higher yields and at lower cost.

Accordingly, it has been found that anthraquinone is advantageously prepared by oxidation of a diphenylmethane derivative in the gaseous phase in the presence of a catalyst prepared from vanadium, a second specified metal preferably ruthenium and optionally a third specified metal, preferably manganese.

The diphenylmethane compounds useful in the present invention are of the formula

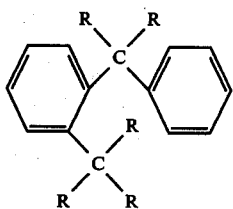

wherein the individual radicals R may be the same or different and each is hydrogen or an aliphatic radical. They may be manufactured by conventional methods, e.g. 2-benzyltoluene may be prepared by the reaction of benzyl chloride and toluene (Ber. 6,906 (1873)). Homologs which are substituted at the methylene group may be obtained analogously, e.g. by reaction of toluene with appropriately substituted styrenes. Preferred starting materials are those wherein each R is the same or different and each is hydrogen or alkyl of 1 to 4 carbon atoms, especially 1, 2 or 3 carbon atoms. The radicals may bear one or more groups and/or atoms which are inert under the reaction conditions, for example alkoxy or alkyl, each of 1 to 3 carbon atoms. Most preferably all of the R groups are hydrogen.

The following are examples of suitable starting materials: 2-butyl-, methoxyethyl-, ethoxymethyl-, 2-isopropyl-, 2-isobutyl-, 2,2-tert-butyl-, 2-propyl-, 2-ethyl-, 2-sec-butyl-, and preferably 2-methyl-diphenylmethane or homologs having as substituents on the methylene group up to two groups each selected from methoxyethyl, ethoxymethyl, methyl, ethyl, isopropyl, n-propyl, isobutyl, secbutyl and n-butyl.

The catalyst of the present invention is prepared from compounds of the specified metal catalyst. The vanadium compound is preferably vanadium pentoxide. Independently of the actual composition, the amount of vanadium in the final catalyst is calculated as vanadium pentoxide. Vanadium compounds which form the pentoxide during the production of the catalyst or during the reaction may also be used. These include such as vanadyl oxalate, vanadyl formate, vanadic acid, vanadyl nitrate, vanadyl acetate, vanadyl tartrate, vanadium oxychloride, vanadium citrate, ammonium vanadate, and vanadium (IV) oxide.

Optionally, the vanadium may be present in the form of a vanadate. Generally, these will be the alkaline earth metal or ammonium vanadates.

Ruthenium may be incorporated into the catalyst by using any suitable ruthenium compound such as the nitrate, chloride, oxides, and Ru(NO)(NO₃)₃.

Rhenium may be incorporated into the catalyst by using any suitable rhenium compound such as the chlorides, bromides, oxides, and complexes thereof with ammonia.

Cerium may be incorporated into the catalyst by using any suitable cerium compound such as the chloride, fluoride, hydroxide, nitrate, oxide, sulfate, and complexes thereof with ammonia.

Niobium may be incorporated into the catalyst by using any suitable niobium compound such as the chloride, bromide, fluoride, iodide, and oxides.

Rhodium may be incorporated into the catalyst by using any suitable rhodium compound such as the nitrate, chloride, iodide, oxide, and complexes thereof with ammonia.

Similarly, the third component, when present, may be incorporated into the catalyst by using suitable manganese, barium, cerium and iron compounds such as the nitrates, chlorides, carbonates, sulfates, oxides, and other such salts.

The ratio of vanadium pentoxide to ruthenium in the catalyst should be in the range of about 2:1 to 50:1, preferably about 5:1 to 30:1, most preferably about 8:1 to 20:1. When manganese is also included in the catalyst, it should be present in amounts up to about the amount of the ruthenium.

The catalysts of the present invention are preferably used together with a carrier material, or support. Suitable supports include such as alumina, silica, alumina-silica, zirconium oxide, silicon carbide, and pumice. Convenient amounts of total catalyst used on the support are from 0.5 to 30, preferably 0.8 to 15, and most preferably 1.0 to 12 percent by weight of catalyst based upon the weight of the support. Preferably, the support has a surface area of less than 10 m2/g.

Independently of the actual metal compounds used to prepare the catalyst, the catalyst is prepared by conventional procedures well-known in the art. Unsupported catalysts may be manufactured, for example, by mixing the compounds or by co-precipitating the metals from aqueous solutions of their salts by means of suitable precipitants and drying the product. The catalyst formed can then be converted to appropriate shapes by such procedure as extrusion.

Preferably, the catalyst is prepared by impregnation of a carrier with the metals in a single or multi-step procedure.

After preparation, the catalyst is advantageously calcined in a stream of air, for example, at a temperature of from about 300° to 800° C.

The oxidation is carried out under conventional conditions of temperature, pressure, oxygen content, etc. Suitable temperatures are about 200° to 700° C., preferably 375° to 475° C., and most preferably 400° to 450° C. The pressure may be either atmospheric or superatmospheric. Oxygen is generally present in excess of that stoichiometrically necessary for the oxidation. It is generally used in the form of air but any mixtures of oxygen and gases which are inert under the reaction conditions, such as argon, water vapor, nitrogen and/or carbon dioxide or flue gas may be used. Preferably the oxygen is used in amounts such that the molar ratio of oxygen to diphenylmethane compound is up to 100:1, most preferably about 40:1 to 70:1. The oxidation is generally performed continuously.

The oxidation may be performed by vaporizing the diphenylmethane compound starting material in a current of oxygen-containing gas heated to more than 150° C. The mixture of vapor and gas is then passed through the bed of catalyst in a reactor at the reaction temperature. Optionally, additional oxygen-containing gases may be fed into the reactor at the same time to bring the $O_2$/diphenylmethane compound ratio to the desired level. Convenient reactors are tubular reactors cooled with a salt bath, fluidization reactors with inbuilt cooling units, or reactors having a plurality of catalyst beds with intermediate cooling means. The end product may then be separated from the reaction mixture by conventional methods, for example the gases leaving the reactor may be passed through one or more separators. The anthraquinone may then, if necessary, be freed from byproducts by washing with water or an alkaline solution. The end product may also be isolated by passing the gaseous reaction mixture into water whereby the anthraquinone is obtained as an insoluble solid. The anthraquinone manufactured by the process of the invention is a valuable starting material for the manufacture of dyes and pesticides, or it may be used in the delignification of cellulose.

The following examples further illustrate the present invention. All parts or percents are by weight unless otherwise specified.

EXAMPLE 1

(a) Manufacture of the Catalyst—One Step Impregnation 3.0 g. of oxalic acid dihydrate is dissolved in 15ml of distilled water by gentle warming. 1.0 g. of vanadium pentoxide is added and dissolved to form a blue solution. 1.42 ml. of 10% ruthenium nitrate solution is added and the solution becomes dark brown. The resultant solution is poured over 8.95 g. of 80×140 mesh alumina-silica support in a flask. The water is evaporated and the impregnated support is removed from the flask. The catalyst is calcined in flowing air for 1 hour at 550° C. and then sieved to remove fines. The 80×140 mesh fraction is then used as the catalyst. It contains about 10% $V_2O_5$ and about 0.5% Ru.

(b) Oxidation

The catalyst manufactured according to (a) is blended with Pyrex glass chips of 80×140 mesh (U.S. Standard Sieve) at the rate of 1 part catalyst/4 parts Pyrex by volume and placed in a fixed bed reactor. The catalyst bed volume is 2.60 cc; the air flow rate is 211 cc/min; the reactor temperature is 440° C.; the 2-methyldiphenylmethane feed rate is 0.0055 g/min and the residence time is 0.3 sec.

The effluent from the reactor is collected and analyzed by gas chromatography.

The yield of anthraquinone is 68% of theory.

EXAMPLE 2

The reaction of Example 1 is repeated except using no ruthenium in the catalyst. The yield of anthraquinone is 61% of theory.

EXAMPLE 3

(a) Manufacture of the Catalyst—Two Step Impregnation Procedure 3.0 g. of oxalic acid dihydrate is dissolved in 15 ml. of distilled water by gentle warming. 1.0g of vanadium pentoxide is added and dissolved to form a blue solution. The solution is poured over 8.95 g. of 80×140 mesh alumina-silica support in a flask. The water is evaporated and the impregnated support is removed from the flask. The catalyst is calcined in flowing air for 1 hour at a temperature of about 400°–550° C. When cool, it is placed in a flask and impregnated with a solution of 2.84 ml. of 10% ruthenium nitrate solution plus 10 ml. distilled water. Again the water is evaporated and the dry catalyst is removed from the flask and calcined in flowing air for 1 hour at a temperature of about 400°–550° C. The desired mesh fraction is then used as the catalyst. It contains a nominal composition of about 10% $V_2O_5$ and about 1.0% Ru.

The procedure is repeated except varying the second metal from nothing to the metals specified in Table I.

(b) Oxidation

Using either the one or two step impregnation procedures, the catalysts of Table I were prepared, the procedure of Example 1 (b) repeated, and the yield of anthraquinone determined by gas chromatography. The results are summarized in Table I below.

TABLE I

| Sample | Catalyst | Temperature | Yield |
|---|---|---|---|
| a | 10% $V_2O_5$ + 0.5% Ru | 440 | 64–68 |
| b | 10% $V_2O_5$ + 0.5% Re | 441 | 64 |
| c | 10% $V_2O_5$ + 0.5% Ir | 421 | 60 |
| d | 10% $V_2O_5$ + 0.5% Pd | 424 | 2 |
| e | 10% $V_2O_5$ | 430 | 60–61 |
| f | 2% $V_2O_5$ + 0.1% Ru | 450 | 65 |
| g | 2% $V_2O_5$ + 0.1% Os | 495 | 59 |

Samples a–e were prepared by a one-step impregnation.
Samples f–g were prepared by a two-step impregnation.

EXAMPLE 4

By using the above described procedures various catalysts were prepared as specified in Table II below.

The catalyst to be tested was prepared and 1.0 ml of it was loaded into a ¼" stainless steel reactor tube and held in place with plugs of Pyrex wool. The pulse micro-reactor was attached to the apparatus and an air flow of 40 cc/min was established through the bed. The reactor was heated by a tube furnace with the temperature being measured by means of a thermocouple held against the outside reactor wall. When the desired reaction temperature was reached, 2-methyldiphenylmethane was injected into the system just upstream from the catalyst bed. After passing through the bed the reaction products and any unconverted 2-methyldiphenylmethane were swept into an on-line gas chromatograph capable of separating the components of the mixture. Relative activities and selectivities of catalysts could be obtained by comparing the GC peak areas of the various components.

The results are given in Table II below.

TABLE II

| Nominal Composition | Anthraquinone Peak Area (× 10⁵) At Two Reacton Temps. | |
| --- | --- | --- |
| | 400° C. | 460° C. |
| 10% V₂O₅ | 3.0 | 4.7 |
| 1% Ru + 10% V₂O₅ | 4.0 | 6.4 |
| 1% CeO₂ + 10% V₂O₅ (0.8% Ce) | 3.0 | 5.0 |
| 1% Nb₂O₅ + 10% V₂O₅ (0.7% Nb) | 3.6 | 3.6 |
| 0.5% Rh + 7% V₂O₅ | 4.9 | — |

Note Rh—V₂O₅ catalyst (a) on different support, (b) 14 × 50 mesh (all others 40 × 80).

EXAMPLE 5

The procedure of Example 3b is repeated using catalysts containing 10% V₂O₅, 0.5% Ru, and the amounts specified below in Table III of a third component. A one-step impregnation procedure is used. The results are:

TABLE III

| Sample | Third Component | Level | Temperature | Yield |
| --- | --- | --- | --- | --- |
| a | Mn | 0.2 | 420 | 70 |
| b | Rb | 0.2 | 490 | 10 |
| c | Ba | 0.2 | 470 | 59 |
| d | Ti | 0.2 | 420 | 62 |
| e | Pd | 0.05 | 390 | 24 |
| f | Bi | 0.2 | 410 | 48 |
| g | Co | 0.2 | 420 | 56 |
| h | Ce | 0.2 | 410 | 68 |
| i | Fe | 0.2 | 430 | 63 |

What is claimed is:

1. In a process for the manufacture of anthraquinone by oxidation of diphenylmethane derivatives of the formula:

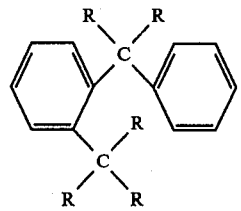

wherein each R may be the same or different and is selected from hydrogen or an aliphatic radical, by means of oxygen in the gas phase in the presence of a catalyst at an elevated temperature, the improvement comprising using a catalyst which is comprised of vanadium, calculated as vanadium pentoxide, and a second metal selected from the group consisting of ruthenium, rhenium, cerium, niobium and rhodium in a weight ratio of about 2:1 to 50:1.

2. The process of claim 1 wherein the weight ratio of vanadium pentoxide to the second metal is about 5:1 to 30:1.

3. The process of claim 1 wherein the weight ratio of vanadium pentoxide to the second metal is about 8:1 to 20:1.

4. The process of claim 1 wherein the oxidation is carried out with a supported catalyst containing about 1 to 30 percent by weight of a catalytically active material, based on the support carrier.

5. The process of claim 4 wherein the support carrier is selected from alumina, silica, alumina-silica, zirconium oxide, silicon carbide and pumice.

6. The process of claim 4 wherein the supported catalyst contains about 0.8 to 15 percent by weight of catalytically active material.

7. The process of claim 1 wherein the oxidation is carried out at from 200° to 700° C.

8. The process of claim 1 wherein the R groups are each selected from hydrogen and alkyl of 1 to 4 carbon atoms.

9. The process of claim 1 wherein the R groups are all hydrogen.

10. The process of claim 1 wherein the second metal is ruthenium.

11. The process of claim 1 wherein the second metal is rhenium.

12. The process of claim 1 wherein the second metal is cerium.

13. The process of claim 1 wherein the second metal is niobium.

14. The process of claim 1 wherein the second metal is rhodium.

15. The process of any one of claims 1, 4, or 9 wherein the catalyst further contains a third metal selected from the group consisting of manganese, cerium and iron in amounts up to the amount of the second metal.